US00PP19945P2

(12) United States Plant Patent
Lim

(10) Patent No.: US PP19,945 P2
(45) Date of Patent: Apr. 21, 2009

(54) SHRUB ROSE PLANT NAMED 'BAIRAGE'

(50) Latin Name: *Rosa hybrida*
Varietal Denomination: BAIrage

(76) Inventor: Peter P. Lim, Bailey Nurseries, Inc., 9855 N.W. Pike, Yamhill, OR (US) 97148

( * ) Notice: Subject to any disclaimer, the term of this patent is extended or adjusted under 35 U.S.C. 154(b) by 0 days.

(21) Appl. No.: 12/151,370

(22) Filed: May 6, 2008

(51) Int. Cl.
*A01H 5/00* (2006.01)

(52) U.S. Cl. ..... Plt./106

(58) Field of Classification Search ..... Plt./106
See application file for complete search history.

*Primary Examiner*—Annette H Para
*Assistant Examiner*—Georgia Helmer

(57) ABSTRACT

A new cultivar of shrub rose, *Rosa* 'BAIrage', characterized by its semi-double flowers that are apricot with a yellow eye when opening and maturing to medium pink with a yellow eye, its everblooming habit, its ability to drop spent flowers cleanly, its rounded habit of medium green, semi-glossy foliage that is resistant to rose blackspot and powdery mildew. 'BAIrage' is readily propagated on its own roots and hardy in U.S.D.A. Zones 4 to 9.

2 Drawing Sheets

Botanical classification: *Rosa hybrida.*
Variety denomination: 'BAIrage'.

The present invention relates to a new and distinct cultivar of *Rosa hybrida.* The new cultivar will be referred to hereafter by its cultivar name, 'BAIrage'. 'BAIrage' is a shrub rose suitable for landscape plantings;

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAIrage', designated as seedling No 00-304 was selected among seedlings derived from a cross made in Yamhill, Oreg. in 2000 between *Rosa* 'Morden Centennial' (not patented) as the female parent and 'TWOadvance' (U.S. Plant Pat. No. 7,078) as the male parent. 'BAIrage' was selected as unique and budded onto understock in August 2000 and reselected by the inventors for its distinct characteristics in 2003.

The new cultivar has been asexually propagated by rooting of softwood cuttings from a plant grown on its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of seven years in Yamhill, Oreg., St. Paul, Minn. and several other test sites in the U.S. These attributes in combination distinguish 'BAIrage' as a unique cultivar of shrub rose.

1. 'BAIrage' exhibits semi-double flowers that are apricot in color with a yellow eye when opening and mature in color to medium pink with a yellow eye. Classified as an apricot blend by American Rose Society standards.
2. 'BAIrage' exhibits a rounded habit with a height of 80 cm to 1 m.
3. 'BAIrage' exhibits medium green, semi-glossy foliage.

4. 'BAIrage' is everblooming and drops its flowers cleanly.
5. 'BAIrage' has shown excellent resistance to rose blackspot (*Diplocarpon rosae*) and powdery mildew (*Sphaerotheca pannosa* var. *rosa*).
6. 'BAIrage' is hardy in U.S.D.A. Zones 4 to 9.
7. 'BAIrage is a vigorous grower and readily propagated by softwood cuttings and grown on its own roots.

The new cultivar of shrub rose can be readily distinguished from its parents and other cultivars. The female parent, 'Morden Centennial', is a shrub rose with fully double flowers that are medium pink in color, dark green glossy foliage, an upright habit, and a plant height reaching up to 1.2 m. The male parent, 'TWOadvance' (U.S. Plant Pat. No. 7,078), is a shrub rose with semi-double flowers that are loose in form and an orange pink blend in color and an upright habit. The cultivars 'Prairie Sunrise' (not patented) and 'AUStamora' (not patented) are close comparison roses. They both have similarity to 'BAIrage' in that they are shrub roses with flowers that open an apricot blend in color and exhibit a similar plant height. They differ from 'BAIrage' in that 'Prairie Sunrise' has fully double flowers that mature to a salmon-apricot color rather than pink and has a recurrent blooming habit and 'AUStamora' has fully double flowers that mature to salmon-pink rather than pink, dark green rugose foliage, an upright rounded habit, and a recurrent blooming habit. In addition, both 'Prairie Sunrise' and 'AUStamora' are susceptible to rose black spot.

BRIEF DESCRIPTION OF THE DRAWING

The accompanying colored photographs illustrate the overall appearance and distinct characteristics of the new shrub rose, 'BAIrage', as grown outdoors in a trial garden in St. Paul, Minn. The photographs were taken of four year-old plants grown on their own roots.

Figure 1:
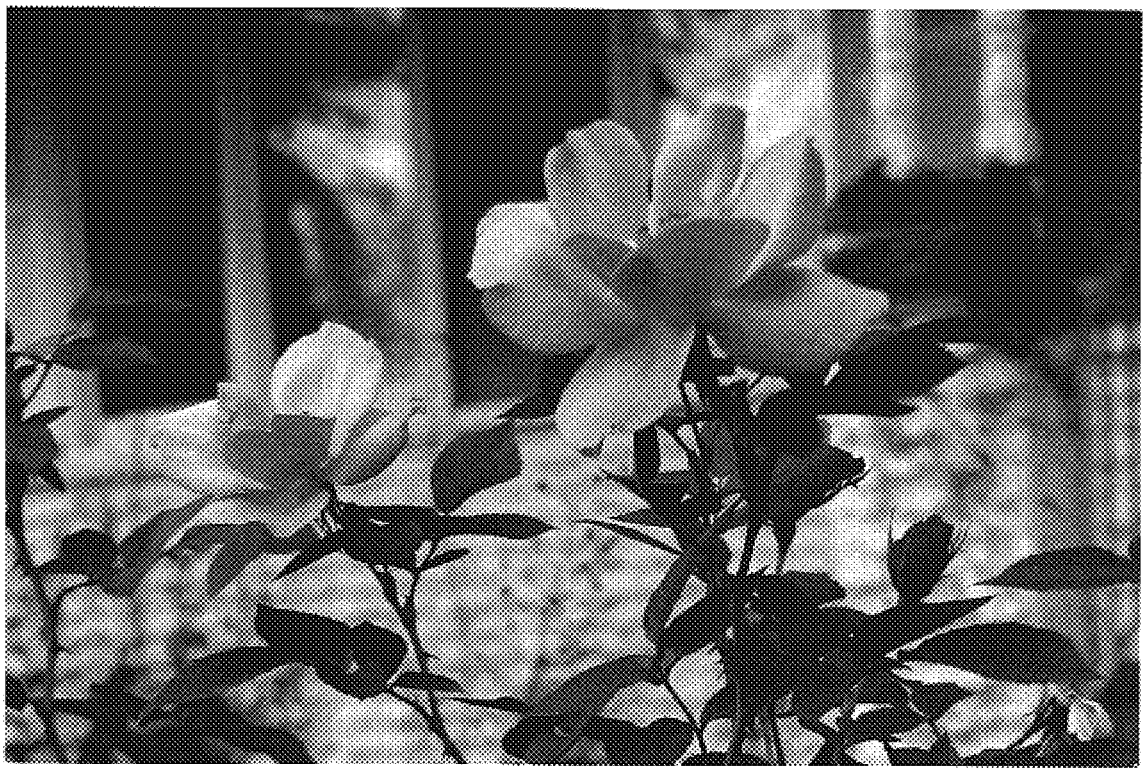
FIG. 1 provides a side view of a newly open flowers and flower buds of 'BAIrage' just prior to opening.
Figure 2:
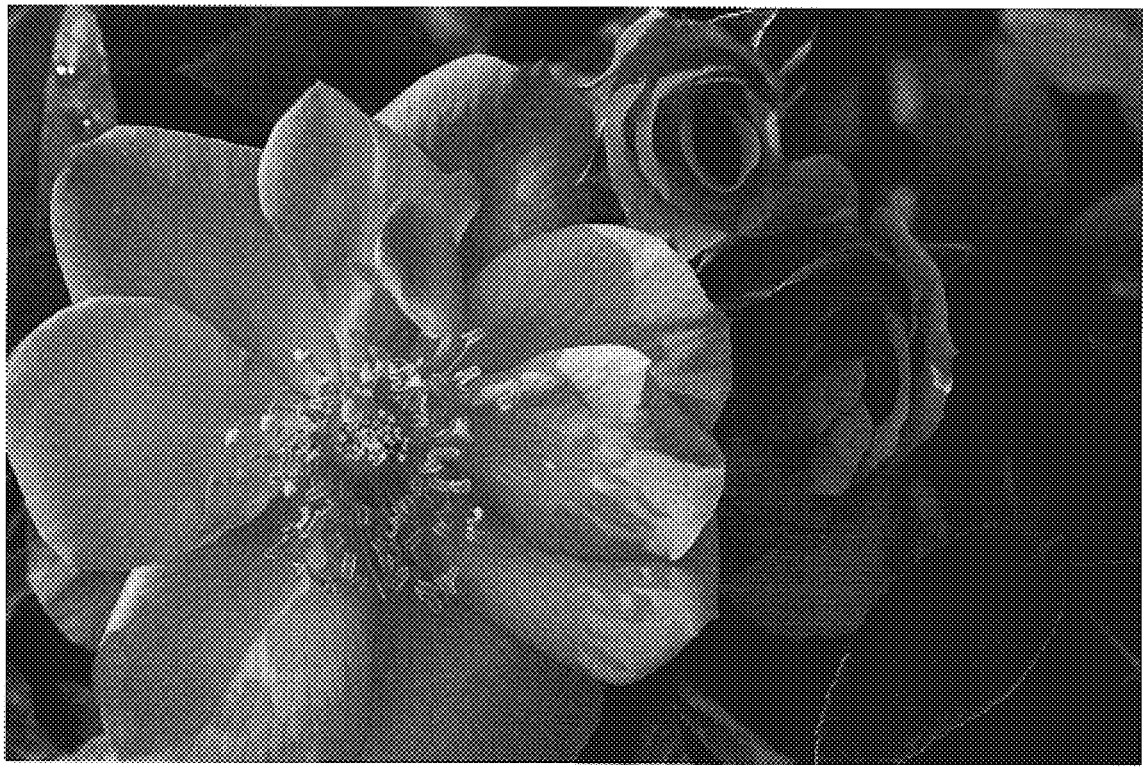
FIG. 2 provides a view of a fully open flower and opening flower buds.
Figure 3:
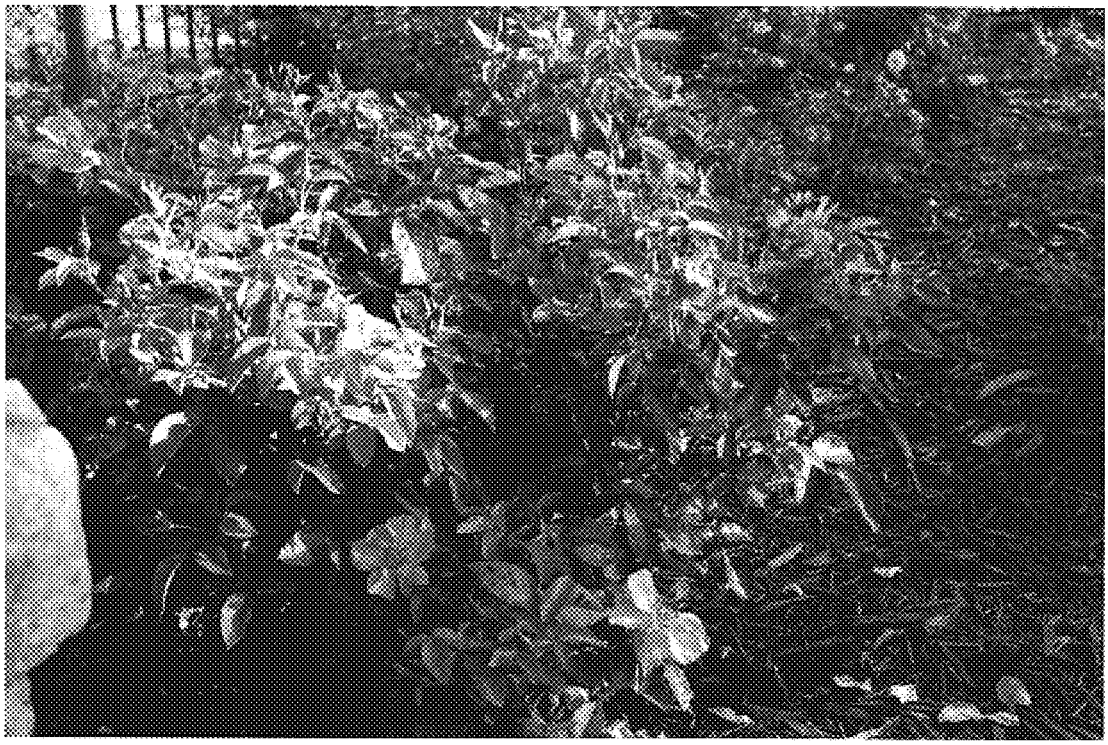
FIG. 3 provides a side view of a plant in bloom and illustrates the plant habit of 'BAIrage'.
Figure 4:
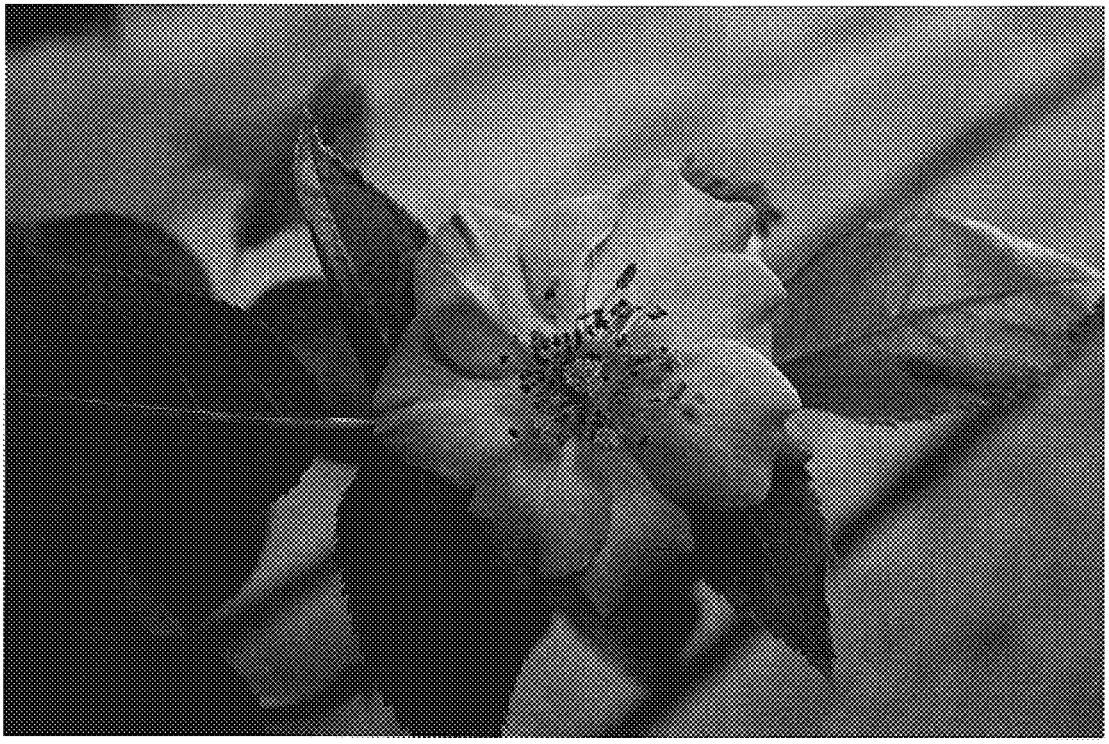
FIG. 4 provides a close-up view of the foliage and a maturing flower of 'BAIrage'.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two and three year-old container plants and five year-old field-grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General Description:

*Blooming habit.*—Everblooming throughout the growing season.

*Plant habit.*—Rounded.

*Height and spread.*—Reaches 80 cm in height and about 1 m in spread.

*Hardiness.*—U.S.D.A. Zone 4 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; 144B, maturing; between 144A and 144B, mature wood; N199B with areas showing through of 199B.

*Stem surface.*—Young; glabrous, mature; glabrous and slightly glaucous, adult wood; bark-like ridges.

*Stem size.*—Average of 4.5 mm in width, up to 80 cm in length with sub laterals an average of 25 cm in length.

*Thorns.*—Triangular with straight tip pointed typically pointed lightly downward, oval base, average of 6 mature thorns per 5 cm in number, an average of 5 mm in length with a base 4 mm in length and 2 mm in width, color is 166B to 172B when mature.

*Branching habit.*—1 to 2 sub laterals per lateral, internode irregular.

Foliage description:

*Leaves.*—Division is odd-pinnate, average of 10 cm in length and 8 cm in width, internode length is an average of 2.5 cm.

*Leaflets.*—5 to 7 (3 at terminal), oval in shape, rounded to broadly cuneate base, acuminate to cuspidate apex, serrated margins with cuspidate tips, glabrous and semi-glossy on upper surface and finely puberulent and dull on lower surface, average of 5 cm in length and 3 cm in width, color: young leaves upper surface; 146A with a very fine margin 178A, young leaves lower surface; 146B suffused with 183B, mature leaves upper surface; 147A, mature leaves lower surface; 147B, venation pinnate, and color or leaflet with midrib on lower surface color of rachis.

*Rachis.*—Average of 6 cm in length and 1 mm in diameter, color of upper surface 144A with 144D between ridges, color of lower surface 144B, surface is glabrous with occasional glands.

*Stipules.*—Long and narrow with auricle facing outward, adnate to petiole, average of 1 cm in length and 5 mm in width, color of upper surface is 137B near margin, 144B near center and 144D on middle ridge, color of lower surface is 138A near margin, 137B near center and 144B on middle ridge, abundant glands on margins and lower surface.

*Petioles.*—Very small (leaflets appear sessile), average of 1 mm in length and diameter, color of upper surface 144A, color of lower surface 137B, glabrous surface.

Inflorescence description:

*Flower longevity.*—About 3 to 5 days, depending on temperature and sunlight exposure.

*Flower type.*—Semi-double (2 rows), shallow cupped.

*Flower size.*—Average of 6 cm in diameter and 4 cm in depth (to a bottom of sepal tips) and 2 cm in depth to base of petals.

*Flower fragrance.*—Slight rose scent.

*Peduncles.*—Stiff, average of 3.5 cm in length and 2.2 mm in diameter, 144A in color, surface is sparsely covered with very fine hairs and numerous glands 178A in color.

*Bracts.*—Not present.

*Flower buds.*—Conical in shape (narrowly ovate), small to medium in size with an average of 2.3 cm in length and 1.3 cm in width prior to opening, 46C in color slightly suffused with N30A, texture is glabrous.

*Sepals.*—5, broadly lanceolate in shape, margin is entire on 2 and foliaceous with glandular appendages in irregular or pinnate pattern on 3, color of upper surface is 138B to 138C with margins 196C, color of lower surface is 138A with margins 196C, upper surface is tomentose, lower surface is glandular, average of 2 cm in length and 7 mm in width, apex is attenuate to leaf-like, base is truncate, aspect is upright in bud stage changing to horizontal when bud opens and reflexed in full bloom.

*Petals.*—10 to 12, drop readily and cleanly, broadly obovate in shape and wavy at apex, upper and lower surface is glabrous, entire margin with occasional notch, cuneate base, rounded wavy apex, average of 3.7 cm in length and 3.6 cm in width, color: opening flowers upper surface; blend of 58D and 33D and blended with 8C on lower third, opening flowers lower surface; blend of 58C and 33C and blended with 8C on lower third, fully open flowers upper surface; blend of 68C and 68D blending with 8D near base in center of petal, fully open flowers lower surface; blend of 68B, 68C and 68D with shadings of 8C to 8D extending irregularly into the middle region from petal spot, end of bloom upper surface; blend of 68D and 62D blending with 8D near base in center of petal, end of bloom lower surface; blend of 68C and 68D with shadings 8D extending irregularly into the middle region from petal spot, petal spot; 8C.

*Receptacle.*—Average of 8 mm in diameter and 1 cm in depth when flower is fully open, urn shaped, glabrous and satiny, 144A in color.

*Pistils.*—Average of 46, stigma is an average of 1 mm in length, an average of 0.4 mm in width and 9D in color, style is an average of 7 mm in length and 9D in color with shadings of 63B, ovary is 2 mm in length and 1 mm width, 155A in color and pilose with very fine hairs about 2 mm in length.

*Stamens.*—Numerous (about 100), curved inward towards pistils, filaments are an average of 1 cm in length and 162A in color, anthers are an average of 2 mm in length, an average of 0.5 mm in width and 162A in color, pollen abundant and 177A in color, occasional petaloid stamens (up to 4 per flower).

*Hips.*—None were observed to mature prior to frost on the plants observed for data collection in Minnesota.

It is claimed:

1. A new and distinct cultivar of shrub rose plant named 'BAIrage' as herein illustrated and described.

* * * * *